United States Patent [19]

Whitson et al.

[11] Patent Number: 4,939,005
[45] Date of Patent: Jul. 3, 1990

[54] TOBACCO FIGURINE

[76] Inventors: Fred W. Whitson, 320 E. Pike St.; Freda G. Saunders, Millcrest Ct. Apt. #5, both of Cynthiana, Ky. 41031

[21] Appl. No.: 393,244

[22] Filed: Aug. 14, 1989

[51] Int. Cl.⁵ .......................... A01N 3/00; A63H 3/00
[52] U.S. Cl. ...................... 428/13; D11/160; D21/155; D21/171; 428/16; 428/17; 446/385
[58] Field of Search ............ D11/160, 164; D21/155, D21/171; 446/72, 385, 386; 428/13, 16, 14, 17

[56] References Cited

U.S. PATENT DOCUMENTS

| | | | |
|---|---|---|---|
| D. 53,626 | 7/1919 | Ziv | D11/160 |
| D. 171,681 | 3/1954 | Burleson | D21/171 |
| D. 219,786 | 1/1971 | Prybella | 428/16 X |
| 1,679,847 | 8/1928 | Webb | 428/16 X |
| 2,636,597 | 4/1953 | Hinz | D21/171 X |
| 4,854,912 | 8/1989 | Koh | 428/16 X |

OTHER PUBLICATIONS

Page 29 and the cover of the 1968 Catalogue of The Mark Farmer Co., Inc., El Cerrito, Calif.

*Primary Examiner*—Henry F. Epstein
*Attorney, Agent, or Firm*—Joseph W. Molasky & Assocs.

[57] ABSTRACT

A figurine or object of art constructed from cured tobacco leaves. The torso or trunk of the object consists of leaves impressed onto a conical support in an overlapping manner where they are arranged to resemble various forms of attire. The figurine appendages are also constructed from leaves which are shaped to resemble known body parts and these are secured by known means. The leaves may differ from one another in size, shape and texture but they have in common a pliancy which allows the creator to produce and re-produce the desired art object by duplicative methods.

13 Claims, 5 Drawing Sheets

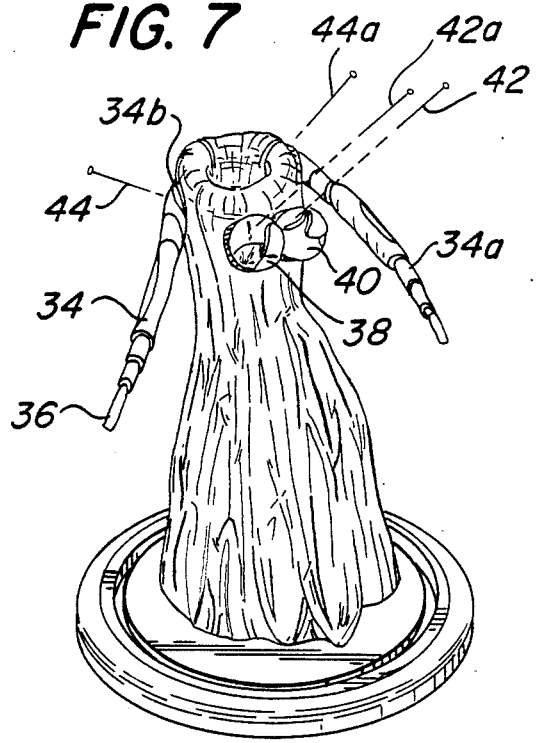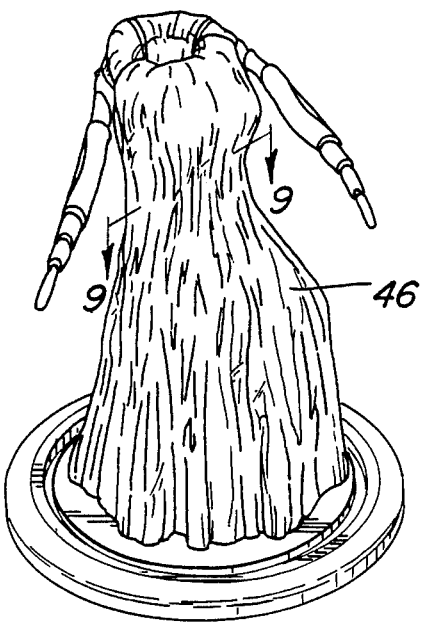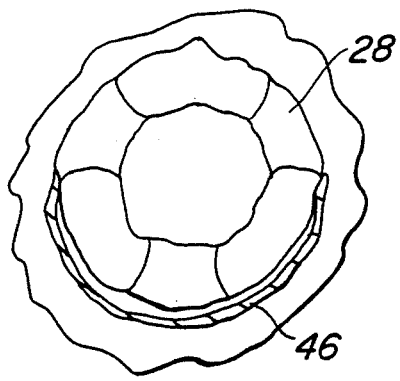

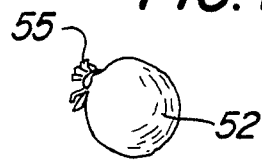
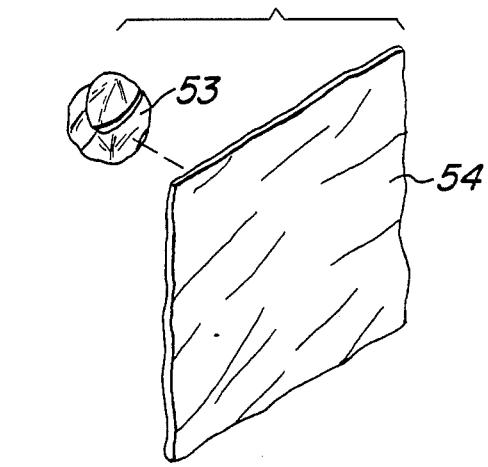
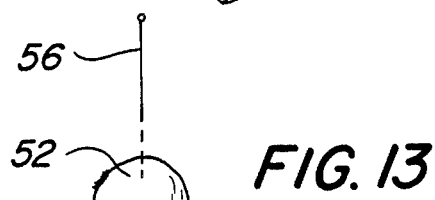
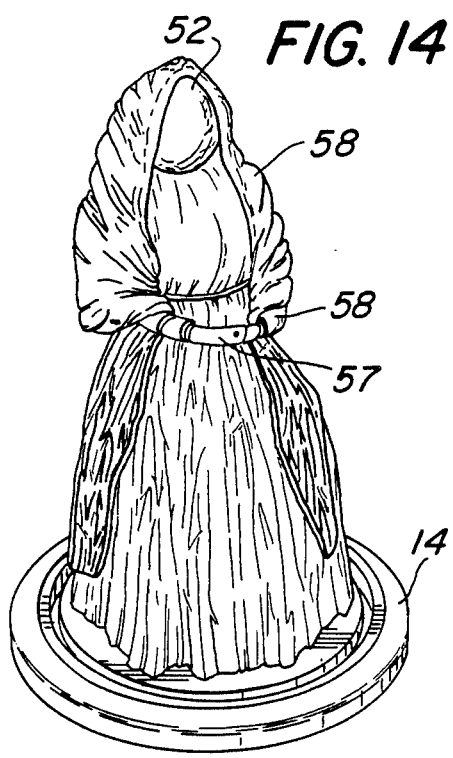

TOBACCO FIGURINE

BACKGROUND OF THE INVENTION

This invention relates to figurines constructed from tobacco leaves and to a method for their manufacture.

The creation of new art forms is usually achieved through the use of known mediums such as paint, clay, stone or materials which have no innate character of their own. These are labor-intensive mediums because the resulting object depends for its value upon the creativity of the artist alone.

However, there are certain materials which by their constitution and essence enhance the beauty of the object sought to be created. Typical of these are, for example, certain stones or gems which, when polished, can be worn as jewelry or can be shaped into artifacts.

Tobacco leaves do not fall into this category because although tobacco is valued by some for its smoking pleasures there is no known precedent for utilizing tobacco as a medium for creating art forms.

Nonetheless, it has been found surprisingly, that the unique texture of cured tobacco combined with its luxurious brown color and manipulable properties can provide the artisan with a medium which is useful in creating art objects.

Accordingly, it is an object of this invention to describe a new art form configured to the likeness of a figurine or statuette and derived entirely from tobacco leaves.

A further object provides for a method by which tobacco leaves can be treated, impressed and transformed into figurines or other art objects.

SUMMARY OF THE INVENTION

This invention relates to figurines or statuettes constructed from cured tobacco leaves which have been dampened or humidified so that they can be facilely manipulated.

The method by which this invention is carried out consists essentially of wrapping the leaves around a cone in an overlapping fashion so as to create a vertically oriented base or trunk which may be configured to simulate the human torso.

Anatomical appendages are portrayed by rolling the leaves in a tubular fashion or by manipulating the leaves into spheres so as to form limbs or other body parts which can be secured to the base or trunk by means which are described hereinafter with particularity.

Thereafter, the fashioned figurine is allowed to dry either in a kiln or by exposure to the atmosphere and it may be spray-lacquered to give it permanency.

If desired, embellishments may be made to the finished article by using additional leaves to form a head covering or a shawl.

These and other modifications of the invention will become apparent from the description of the Drawings and Preferred Embodiments set forth below.

BRIEF DESCRIPTION OF THE DRAWINGS

FIG. 7 shows the arms and breasts being attached to the torso of the figurine.

FIG. 8 depicts the covering of the breasts with a vertically arranged leaf of tobacco.

FIG. 9 is a sectional view 9—9 taken through the waist of the figurine.

FIG. 10 illustrates the placement of a belt around the waist of the figurine.

FIG. 11 shows the formation of a ball of tobacco representing the head in juxtaposition to a smooth surfaced section of tobacco.

FIG. 12 illustrates the placement of the smooth section around the ball to furnish smooth facial features for the figurine's head.

FIG. 13 depicts the placement of the head upon the torso of the figurine.

FIG. 14 shows the placement of a shawl about the shoulders of the figurine.

DESCRIPTION OF THE PREFERRED EMBODIMENTS

Figure 1:
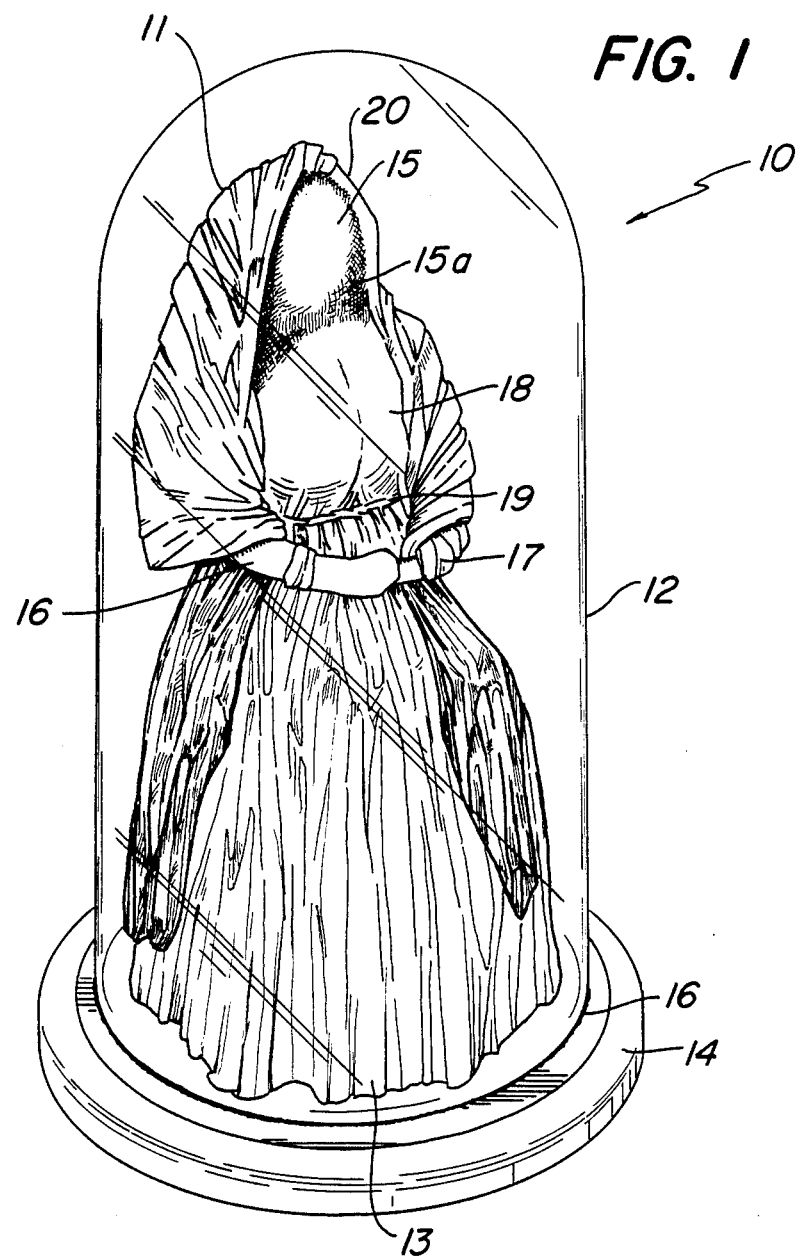
FIG. 1 is a front view of the figurine of the invention which is maintained in an air tight container.
Figure 2:
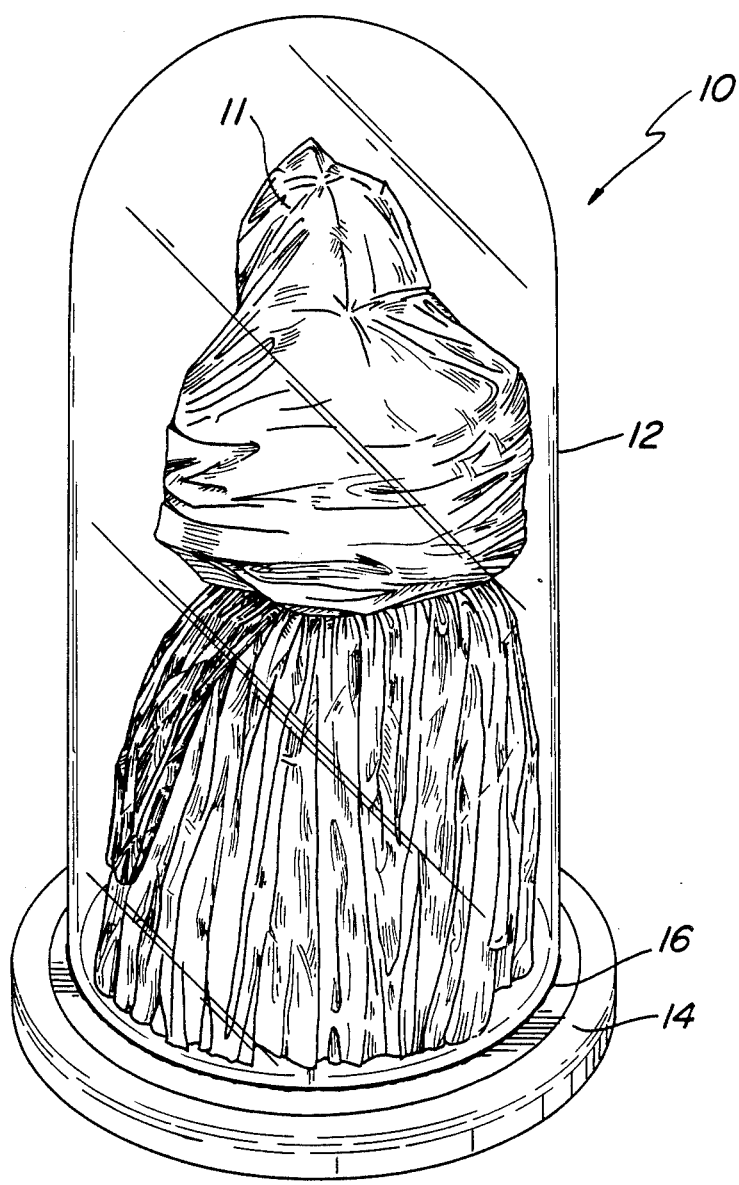
FIG. 2 is a rear view of the figurine of FIG. 1.

FIGS. 1 and 2 illustrate the front and rear views of an art object 10 in the form of a statuette or figurine 11 made from an organic material consisting of a dark burley tobacco. Burley tobacco, which is a broad leaf plant, is a type of tobacco indigenous to certain areas of the United States such as West Virginia, Tennessee and Kentucky. The figurine 11 whose physical dimensions are approximately $5\frac{1}{4}$ inches by $9\frac{1}{2}$ inches high is maintained after its construction in an $11\frac{1}{2}$ inch high sealed glass dome container 12 in order to prevent the leaves from crumbling and to maintain them in an integral state. In order to accomplish this the glass dome 12 is permanently positioned within a $5\frac{1}{4}$ inch diameter groove 16 formed in a 7 inch diameter wooden base 14 by use of an appropriate silicon based adhesive. As will be described in detail hereinbelow, the figurine 11 is constructed in parts or sections consisting of the trunk or torso including the dress 13, the appendages comprising the head 15, the arms 16, 17, the bosom 18, the belt 19 and the shawl 20. Hair 15a in the form of narrow tobacco strips is also furnished around the head 15 to enhance the feminine appearance of the figurine 11.

The figurine construction is initiated by growing burley tobacco leaves to full growth after which they are cut, and then hung for curing purposes in a weather sheltered environment such as a barn. The tobacco leaves while curing turn color from green to a rich brown hue and it is the deep brown color that contributes to the uniqueness and beauty of the figurine of FIGS. 1, 2. After the tobacco leaves have completed the curing process, approximately fifteen to twenty in number, which are required to construct the figurine 11, are maintained in a high humidity atmosphere in order to make the leaves pliable preparatory to being manipulated upon by the fingers and hands of the artisan.

Figure 3:
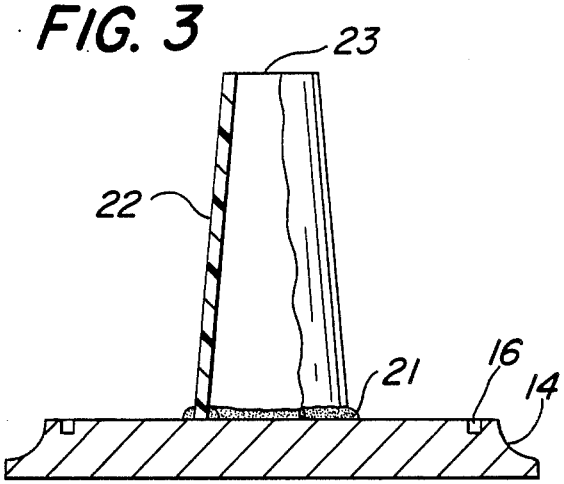
FIG. 3 is a view of a truncated cone which is the form used for attaching various tobacco leaves in making the figurine.

The view of the conical section 22 in FIG. 3 illustrates the initial structure which is utilized in fabricating the figurine 11. The cone 22 is a plastic truncated member that is approximately $4\frac{1}{2}$ inches in height with a $1\frac{1}{2}$ inch diameter opening 23 at the top. The top opening 23 of the truncated cone 22 approximately locates the waist height of the figurine 11. The cone 22 is joined to the base 14 at its approximate center by the silicone adhesive 21 so that the two are integrally joined to one another to give the figurine 11 stability when it is completed and housed within the glass dome 12. Groove 16 is used to receive an edge of the glass dome 12 of FIGS. 1, 2.

Figure 4:
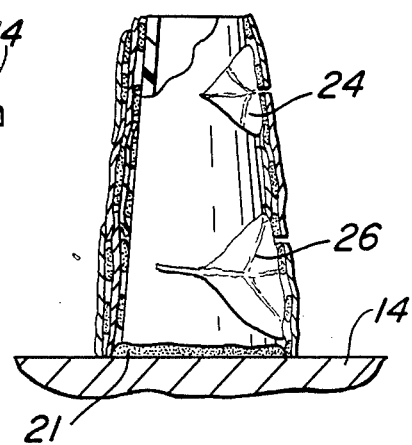
FIG. 4 illustrates an attachment of the leaves in both a horizontal and vertical configuration to the cone.
Figure 5:
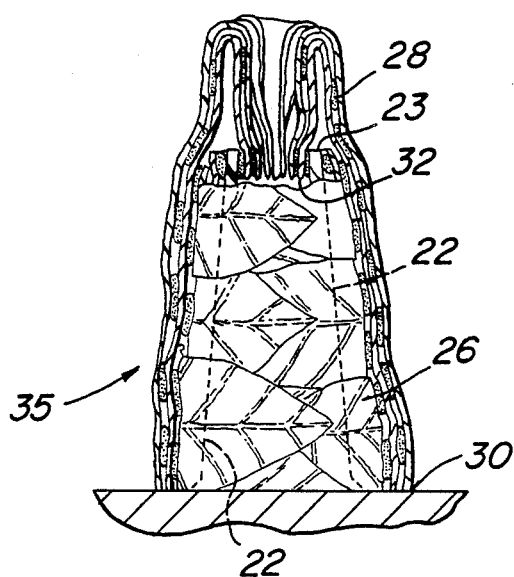
FIG. 5 illustrates the attachment of the vertical leaves to the top opening of the truncated cone.

After the cone 22 is firmly in place upon the base 14 several tobacco leaves 24, 26, whose number is dependent upon the leaf size, are glued with a horizontal orientation to its exterior surface as seen in FIG. 4. After placement of the horizontal leaves a plurality of leaves 28 which are approximately fifteen in number depending upon their respective sizes are oriented in a vertical fashion about the cone 22 and over the horizontally placed leaves 24, 26. The leaves 28 are positioned upon the cone 22 so that their respective tips 30 are at the bottom of the cone 22, whereas, the stem endings 32 are fixedly located within the top opening 23 as seen in FIG. 5. The vertical leaves 28 are brought vertically above the opening 23 and then the stem endings 32 are reversed to bring them within the conical opening. The stems 32 remain fixed in the opening 23 due to its small diameter which allows all to be bundled together in a tight manner. After the horizontal leaves 24, 26 and the vertically oriented leaves 28 are in place, the cone 22 is completely covered which causes a build-up beyond its outline. The placement of all of the leaves 24, 26, 28 upon the cone 22 completes the formation of the torso or trunk 35 of the figurine 11 and the artisan is in a state of readiness to complete other aspects of the figurine construction.

Figure 6:
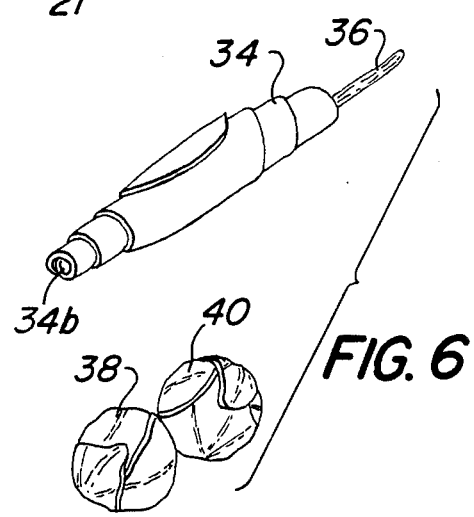
FIG. 6 depicts the formation of the arms and breasts for the figurine.

Various appendages such as the arms, head and breasts are also constructed for eventual attachment to the torso 35, and their formation is illustrated in FIGS. 6, 11, 12. With reference to the upper level of FIG. 6, the formation of an arm 34 by means of a tobacco leaf is shown. To fabricate the arm 34 a leaf of tobacco is cut from each end into a rectangle (not shown) of about 8 inches in length. The cut portion of the leaf near the stem end that is not part of the rectangular section which has a length of about 3 inches is stripped of all tobacco in order to leave a bare stem section 36. The rectangular piece is turned to the right side up position and the stripped stem section 36 is glued to one end leaving one inch extending from the end of the rectangle. Glue is put over the entire piece and rolled up completely around to form the arm 34. The process is similarly repeated to form the second arm 34a (see FIG. 7).

Referring further to the bottom portion of FIG. 6, two marble size spheres 38, 40 are depicted which are used in the figurine 11 for forming the two breasts. Each sphere 38, 40 is formed by stripping a leaf of tobacco and rolling them up into spheres. It is not necessary that the spheres 38, 40 have a smooth surface since an adhesive is applied to their exterior surfaces and appropriately attached with pins 42, 42a to the exterior surface of the torso 36 as seen in FIG. 7 until the adhesive dries. The arms 34, 34a are also attached to the torso 35 by applying adhesive to one end 34b and connecting the respective pieces by straight pins 44, 44a. After the adhesive has dried, the pins 42, 42a, 44, 44a are removed since they are no longer necessary.

A well formed leaf 46 that has been selected from the fifteen to twenty leaves that were originally selected to complete the figurine 11 is utilized to cover the front of the torso 35 as shown in FIG. 8. The leaf 46 is selected to cover the breasts 38, 40 as seen in FIG. 7 and is draped around the front portion of the figurine 11 to cover approximately one-half of its diameter as may be viewed in the sectional view of FIG. 9. The outer leaf 46 is glued onto the previously arranged vertical leaves 28 positioned around the cone 22 (see FIG. 5).

FIG. 10 depicts another step of the fabrication of the statuette and consists of placing a belt 50 around the waist and under the bosom of the figurine 11. The belt 50 is a bare stem of a tobacco leaf that has been stripped of all of its tobacco. The stem 50 is wrapped around the exterior of the figurine 11 in the location that approximates the waist area, and it is tied in the back in conjunction with a dab of adhesive in order to maintain the tie (not shown).

The head 52 of the figurine as depicted in FIG. 12 is made by cutting 5 inch by 5 inch square section 54 as in FIG. 11 from a well formed tobacco leaf. The section 54 is then set aside and a sphere 53 approximately 1½ inches in diameter is fabricated either by utilizing scraps of tobacco, or by stripping a leaf from its stem and then squeezing the material together to construct the sphere 53. After the sphere 53 is constructed it is covered with glue and the square section 54 is wrapped around it to make a smooth surfaced sphere 52 which simulates the human head. After the square section 54 has been joined with the sphere 52 and pulled smooth, the excess portion 55 is gathered at the back and twisted together. When these steps have been performed the spherical head 52 is set aside to allow the glue to dry.

In FIG. 13 there is illustrated the joining of the head 52 to the torso 35 of the figurine 11. A small portion of adhesive is applied to the head 52 where it is to be placed in the opening 60 (see FIG. 10) and upon the collar portion 62 with the twisted part 55 being oriented rearwardly. Needles such as needle 56 are placed through the doll head 52 so that they pierce the collar portion 62 of the torso 35 to hold it in place until the adhesive dries. As many as four needles are placed through the head 52 in a manner that is invisible to the observer when the figurine is completed. Small tobacco scraps that simulate human hair are added (not shown) to the top and sides of the head 52 to enhance the features of this figurine 11.

In order to complete the formation of the figurine 11, a shawl or cape 58 is placed over its head 52. The cape 58 is formed by taking a smooth tobacco leaf and folding it in half at the stem with the under portion extending outwardly. Adhesive is placed on the top of the leaf and the orientation is then reversed and the largest part is placed directly over the head. The ends of the leaf are tucked between the arms 16, 17 and the torso 35. The hands 57, 58 are finally glued and pinned together in front of the figurine 11. The cape 58 is observed to ascertain if it has a proper fit, and the ends may be trimmed if necessary to achieve a proper fit.

To complete the figurine 11 the leaves 28, 46 of the skirt which formation was described in FIGS. 5, 8 are turned upwardly until they are even with the wooden base 14. Each leaf is turned one at-a-time making the front leaf 46 (see FIG. 8) the last one to be folded under. This gives the figurine 11 a smooth and finished appearance. The folding under of the skirt is accomplished with adhesive and pins and the latter may be removed when the cement has dried. All other pins may also be removed after the cement has dried so that the figurine 11 is formed essentially out of a natural product.

The FIG. 11 may be given a finished appearance by spraying the doll with a light lacquer finish and allowing it to dry.

Although the invention has been described as being fabricated in a certain series of sequential steps, it is well understood that others may vary from the described mode without departing from the invention.

This invention has been described by reference to precise embodiments but it will be appreciated by those skilled in the art that this invention is subject to various modifications and to the extent that those modifications would be obvious to one of ordinary skill they are considered as being within the scope of the appended claims.

What is claimed is:

1. A figurine comprising:
   (a) a plurality of pliable tobacco leaves;
   (b) a plurality of sections made of said tobacco leaves which when combined with one another form said figurine; and
   (c) an air-tight container for displaying said figurine, said container maintaining said leaves in an integral state.

2. The figurine in accordance with claim 1 wherein said leaves consist of cured burley tobacco.

3. The figurine in accordance with claim 1 and further comprising:
   (a) a form; and
   (b) said sections being fabricated by draping and attaching said leaves around and over said form and by fabricating geometrical members for attachment to said form.

4. The figurine in accordance with claim 3 wherein one of said geometrical members is spherical in shape.

5. The figurine in accordance with claim 3 wherein another of said geometrical member comprises a tobacco leaf which is rolled up along its axially oriented stem.

6. The figurine art object comprising:
   (a) a plurality of cured tobacco leaves which have been made pliable in high humidity;
   (b) a member which is relatively shaped to conform to a general outline of said figurine as a form upon which are placed several of said plurality of pliable leaves for constructing the torso of said figurine;
   (c) a plurality of spherical shapes made from certain of said plurality of leaves and positioned upon said torso to form the head and bosom of said figurine;
   (d) dual leaves of said leaf plurality rolled up along their respective length dimensions to form arms;
   (e) said arms being attached to said torso; and
   (f) a singular leaf placed upon the frontal area of said figurine for attachment to said form and in order to cover said bosom.

7. The figurine formed in accordance with claim 6 embellished by a tobacco leaf stem to represent a belt around said torso.

8. The figurine art object in accordance with claim 6 further comprising a transparent air-tight container in which said figurine is housed.

9. The figurine art object in accordance with claim 6 which further comprises attaching leaves about the torso to form a shawl.

10. The method of forming a figurine from cured tobacco comprising the steps of:
    (a) curing said tobacco leaves;
    (b) maintaining said leaves in a moist environment for causing said leaves to become pliable;
    (c) positioning a plurality of said pliable leaves around a form for constructing the torso of said figurine;
    (d) forming three spheres from said tobacco leaves;
    (e) attaching two of said spheres to the upper part of said torso to form the breasts of said figurine;
    (f) positioning at least one tobacco leaf over said two spheres;
    (g) attaching one of said three, spheres to said torso to form a head for said figurine;
    (h) rolling at least two leaves about their respective stems to form the arms of said figurine and attaching said rolled leaves to said form.

11. The method in accordance with claim 10 including the step of positioning a belt around said torso under said bosom.

12. The method in accordance with claim 10 including the step of positioning a tobacco leaf around said head and over said shoulders to form a shawl.

13. The method in accordance with claim 10 including the step of mounting said figurine in an air-tight glass container.

* * * * *